US007271911B2

(12) United States Patent
Muehlig et al.

(10) Patent No.: US 7,271,911 B2
(45) Date of Patent: Sep. 18, 2007

(54) METHOD FOR THE QUANTITATIVE MEASUREMENT OF THE PULSE LASER STABILITY OF SYNTHETIC FUSED SILICA GLASS

(75) Inventors: Christian Muehlig, Jena (DE); Wolfgang Triebel, Jena-Cospeda (DE); Siegfried Kufert, Kahla (DE); Sylvia Bark-Zollmann, Jena (DE); Ute Natura, Jena (DE); Frank Coriand, Jena (DE)

(73) Assignee: Schott Glas, Mainz (DE)

( * ) Notice: Subject to any disclaimer, the term of this patent is extended or adjusted under 35 U.S.C. 154(b) by 314 days.

(21) Appl. No.: 10/887,421

(22) Filed: Jul. 8, 2004

(65) Prior Publication Data

US 2005/0007595 A1 Jan. 13, 2005

(30) Foreign Application Priority Data

Jul. 9, 2003 (DE) ............................... 103 31 589

(51) Int. Cl.
*G01N 21/00* (2006.01)

(52) U.S. Cl. .................................................... 356/432

(58) Field of Classification Search ................ 356/432; 65/378
See application file for complete search history.

(56) References Cited

U.S. PATENT DOCUMENTS 6,075,607 A 6/2000 Jinbo et al.
6,226,128 B1 * 5/2001 Shiozawa ................... 359/642
6,320,700 B2 11/2001 Shiozawa
6,734,970 B2 * 5/2004 Wang ......................... 356/388

FOREIGN PATENT DOCUMENTS

DE 101 39 906 6/2000
DE 100 50 349 5/2002
EP 0 866 331 9/1998

OTHER PUBLICATIONS

P. Karlitschek, Photodegradation and Nonlinear Effects in Optical Fibers Induced by Pulsed UV-Laser Radiation, Optics Communication, 116 (1995) Apr. 15, Nos. 1-3, Amsterdam, NL, pp. 219-230.*
W. Triebel et al.; "Simultaneous measurement of bulk absorption and fluorescence in fused silica upon ArF laser irradiation"; Proc. of SPIE, vol. 4779, pp. 107-116, 2002.

* cited by examiner

*Primary Examiner*—Tarifur Chowdhury
*Assistant Examiner*—Isiaka O Akanbi
(74) *Attorney, Agent, or Firm*—Jordan and Hamburg LLP

(57) ABSTRACT

The present invention refers to a method for the quantitative measurement of the pulse laser stability of synthetic fused silica, whereby this method avoids time-consuming and demanding measurements and saves material. First, the absorption of fused silica is measured for different energy densities, and a non-linear function $\alpha_1(H)$ is determined on the basis of the measured values. Second, the fused silica is subject to radiation with a higher energy density up to the point at which a constant absorption value is achieved. In the following, the absorption of the fused silica is measured at different energy densities, and a non-linear function $\alpha_2(H)$ is determined. The difference between the two non-linear functions indicates the increase of absorption that depends on the energy density.

4 Claims, 3 Drawing Sheets

Figure 1:
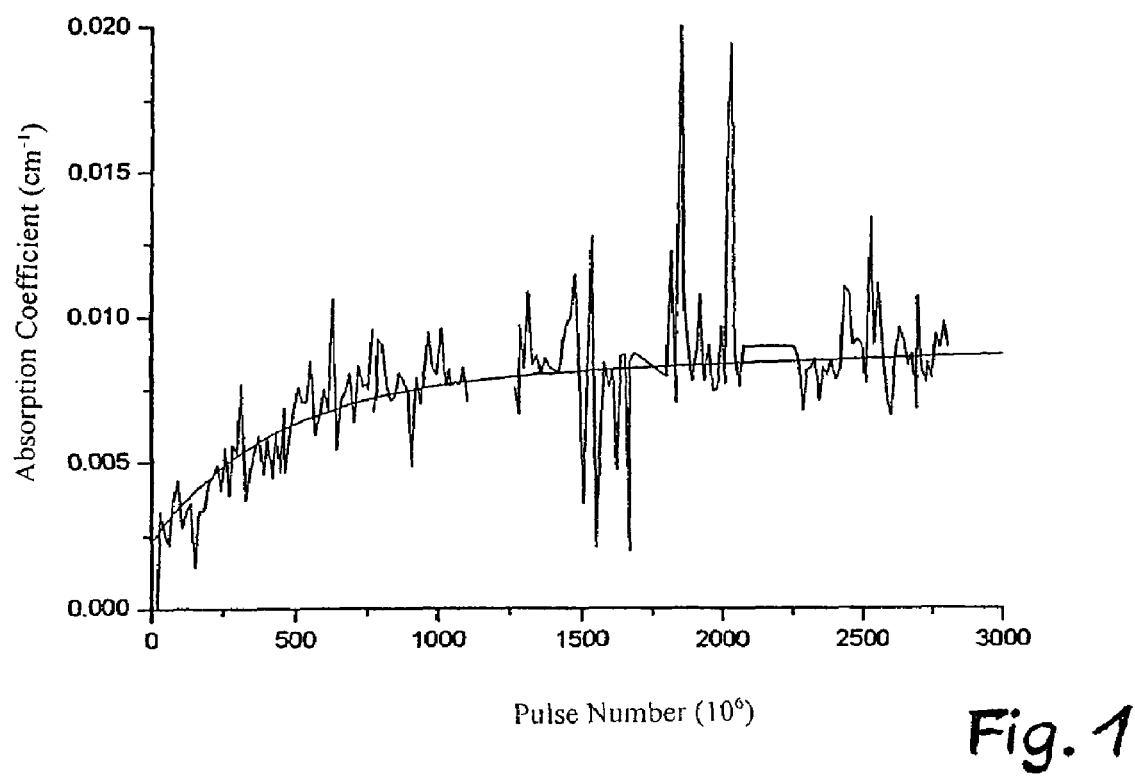

METHOD FOR THE QUANTITATIVE MEASUREMENT OF THE PULSE LASER STABILITY OF SYNTHETIC FUSED SILICA GLASS

DESCRIPTION

The invention refers to a method for the quantitative measurement of the pulse laser stability of synthetic fused silica by means of a direct absorption measurement according to the species of the disclosure.

It is well-known that the determination of the long-time stability of fused silica is preformed by means of long-time or marathon irradiation nowadays combined with the simultaneous transmission measurement. For this purpose, the lithography irradiation requirements with low energy densities of about 1 mJ/cmd² or $\leq 1$ mJ/cm² at repetition rates of 1-4 kHz applied in accordance with a future field of application. Due to the low absorption, sample lengths of >75 mm are required to ensure a sufficient accuracy of the transmission measurement. The marathon measurements shall confirm both the achievement of a constant, acceptable value after a long phase of absorption increase and the correlation to models of long-time ageing of fused silica. Depending on the energy density pulse numbers of several $10^9$ and —for appropriate repetition rates and permanent irradiation—exposure times of some weeks are required for doing this. The disadvantage of this method is the fact that apart from high operation and material costs required for the study, e.g. one laser rube is necessary per examination (afterwards it is unusable), the samples can show irreversible structure changes (microchannels) even before reaching the demanded exposure period due to the required sample length. These changes make the evaluation of the measured results for model formation and technology development impossible.

Therefore, the task of the invention is to specify a procedure for determining the long-time stability of synthetic fused silica which allows to considerably reduce the time and costs of examination in particular by using short sample lengths (ca. 10 mm).

According to the present invention, this task is solved by the elements of the description.

Thus, the inventive procedure aims to measure a fused silica sample for its absorption at different or continuously increasing energy densities, e.g. 5-20 mJ/cm². These measurements result in the characteristic function $\alpha_1(H)$ of the material before long-term ageing. Due to the energy transmission, this function reflects a non-linear dependency of the absorption coefficient on the light energy density. The subsequent permanent irradiation of an energy density being constant up to reaching a constant absorption value and having a value, e.g. 20 mJ/cm², which is considerably higher than the ones of the state of the art, than the common values of optic lithography in typical application, which is <5 mJ/cm², allows the reduction of the pulse number very effectively. According to the state of the art, this pulse number would be required over a long phase of absorption increase till reaching the constant absorption value. Thanks to the short sample length, the development of additional irreversible changes such as microchannels can be avoided. The absorption measurement for different energy densities subsequent to the permanent irradiation is preferentially performed after continuously decreasing the energy densities and leads to a second characteristic function $\alpha_2(H)$, from which the first characteristic function $\alpha_1(H)$ is subtracted. The resulting difference presents the intensity-dependent absorption increases for different light energy densities. In this way it is possible to determine the increase of absorption even for lithography-relevant intensities.

Thus the nature of the processes acting in the defect generating and curing in synthetic fused silica exposed to UV/DUV pulse laser light offers the possibility to shorten the marathon measurements mentioned above, for example by increasing the light intensity. But, by applying state of the art technologies this would lead to an acceleration of the undesired irreversible changes (formation of microchannels). The application of direct absorption measurement methods combined with the inventive procedure allows to operate with samples of short lengths (10 mm instead of 75 mm and more) and to gain comparable study results concerning the absorption increase with reference to the state of the art. In particular, the method of laser induced diversion (e.g. by an LID construction according to DE 101 39 906) offers a great advantage. The inventive procedure offers a favorable development, if the permanent irradiation and thus the pulse laser stability measurement of the sample is performed in the range of low temperatures (T<200 K). It is part of the invention that the determination of the reached saturation of the development of absorbing defect centers cannot only be carried out by absorption or fluorescent measurements but also by transmission measurements.

Subsequently, the results of a comparison of the examinations according to the state of the art and of the inventive procedure are explained by using six diagrams. They show:

FIG. 1 the results of a marathon measurement according to the state of the art

Figure 2:
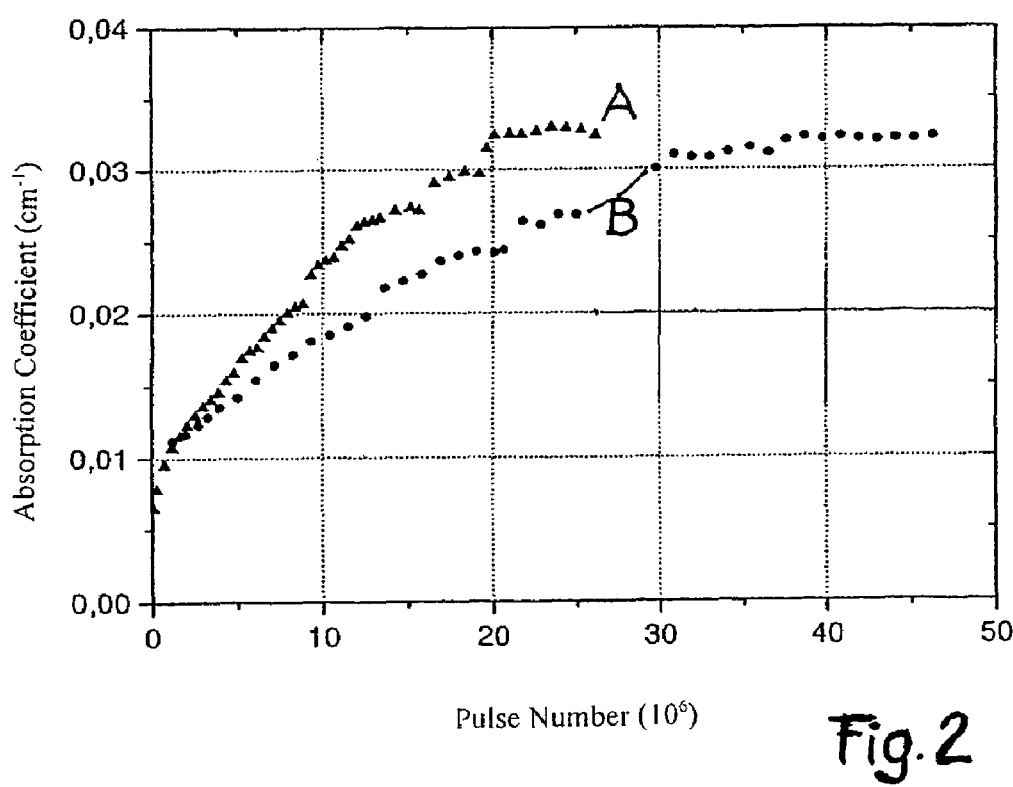
Figure 3:
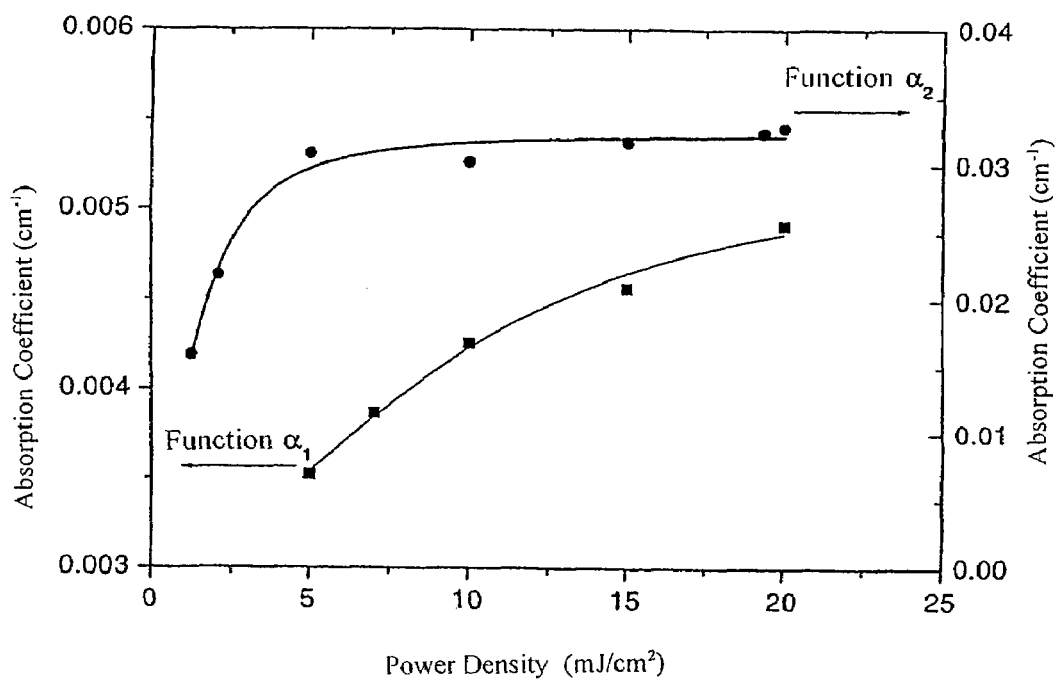

FIG. 2 the results of a permanent irradiation for two samples according to the inventive procedure for two energy densities being significantly higher than in FIG. 1, FIG. 3 the dependency on the energy density for a permanent irradiation performed according to FIG. 2.

Figure 4:
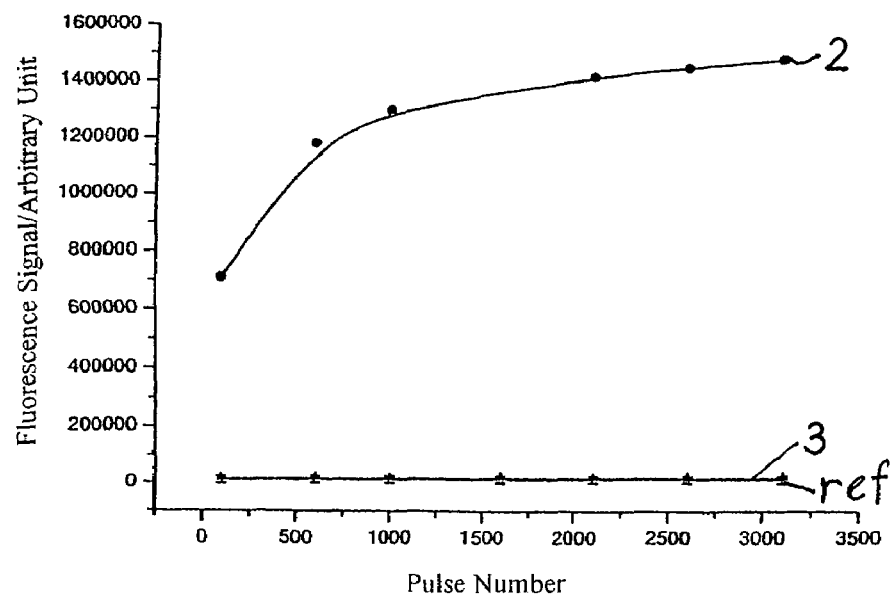

FIG. 4 the dependency of the LIF bands at 650 nm being characteristic for fused silica exposed to pulse laser light in dependency on the hydrogen content at room temperature.

Figure 5:
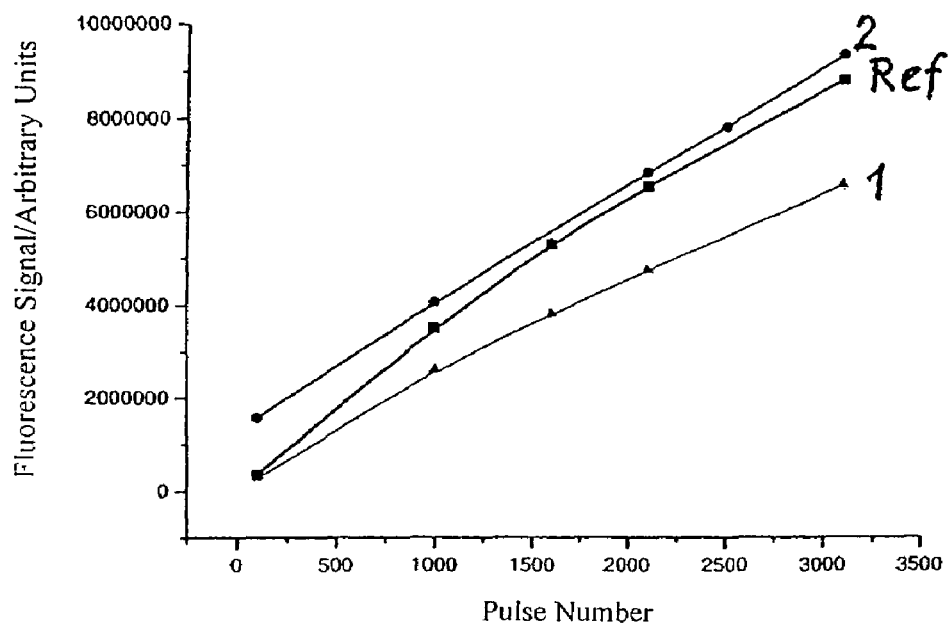
Figure 6:
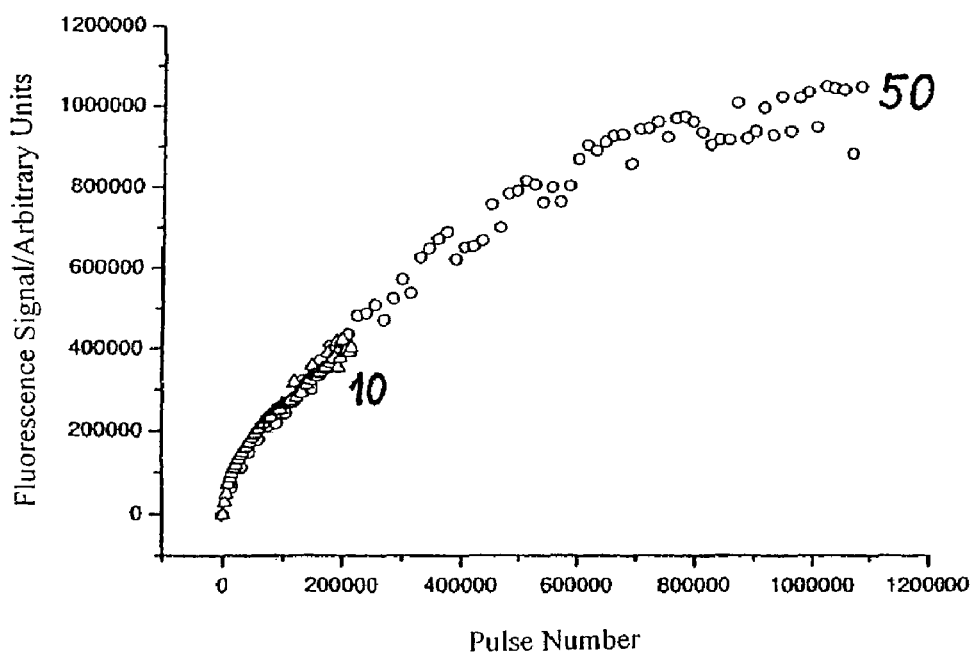

FIG. 5 the behavior of samples with different $H_2$ contents at low temperatures and FIG. 6 the pulse-number-dependent development of a LIF signal of 650 nm at different repetition rates at low temperatures.

For the state-of-the-art investigation of a selected fused silica sample having a hydrogen content of $>10^{17}$ Mol/cm³ by means of a pulsed laser with a repetition rate of 1000 Hz, $2.75 \cdot 10^9$, laser pulses of an intensity of 1.3 mJ/cm² have been applied during 24 h over a period of 32 days. The result is a measurement point distribution—demonstrated in the diagram in FIG. 1—which generally shows a constancy of the induced absorption starting from $2 \cdot 10^9$ pulses.

The irradiation of an equivalent fused silica sample performed according to the inventive procedure was made by an energy density of 20 mJ/cm², with a repetition rate of only 250 Hz for a period of about 30 h, corresponding to $2.7 \cdot 10^7$ pulses. Subsequent to the irradiation, an intensity variation followed to determine the absorption values for other intensities. The irradiation of a further sample performed according to the inventive procedure was made by using the following irradiation parameters: energy density of about 10 mJ/cm², repetition rate of 300 Hz, period of exposure of about $4.6 \cdot 10^7$ pulses, corresponding to about 43 h. The measurements to the inventive procedures are presented as point series A and B in the diagram of FIG. 2.

In case of irradiation, the result is the dependency of the energy density of the point series A demonstrated in FIG. 3. In this figure a data series is presented by points and the function $\alpha_2$ derived from them is presented by a line. The comparison of the absorption values of FIGS. 1 and 3 after the termination of irradiation, i.e. after reaching a constant absorption value for the energy density of irradiation, leads to comparable results for the two examples for the intensity of 1.3 mJ/cm². Moreover, a function $\alpha_1$ gained from the data series is given in FIG. 3. The course of this function differs significantly from the one of function $\alpha_2$. The absorption increase depending on the energy density can be determined from the difference of the non-linear functions $\alpha_1(H)$ and $\alpha_2(H)$. To get a function $\alpha_1$ or $\alpha_2$, we refer to Proc. of SPIE, vol. 4779, 2002, pp 107-116.

For the laser-induced fluorescence measurement (hereinafter referred to as LIF measurement) at room temperature, the development of the LIF bands at 650 nm, being characteristic for the development of defect centers (NBOH centers), considerably depends on the hydrogen content ($H_2$) under pulse laser irradiation, i.e. on the curing of defect centers between two laser pulses. A high hydrogen content allows a very efficient curing. Practically no increase of the LIF intensity results from this for the reference sample ($H^2=3.5\cdot10^{18}$ cm$^{-3}$) and the sample 1 [$H_2=(1.5-2.0)\cdot10^{18}$ cm$^{-3}$] according to FIG. 4 at 650 nm. Regardless of the pulse number, the fluorescent signals of the two samples are always the same. But the sample 2 with $H_2<10^{16}$ cm$^{-3}$ has a $H_2$ content that is lower by more than 2 magnitudes. Therefore, this sample exhibits a considerably lower curing effect being expressed in the pulse-number-dependent increase of the NBOH centers.

If the same measurements are taken at lower temperatures (T<200° K), e.g. at −185° C., the behavior of the samples changes. Due to the low temperatures the mobility of the molecular hydrogen is drastically reduced, it is "frozen". This effect mainly prevents the irradiation-induced defects from curing. Regardless of the $H_2$ content, the three samples behave in the same way, that is like the sample 2 having a low $H_2$ content at room temperature.

This fact is demonstrated in FIG. 5 which presents like FIG. 4 the examination results for all the three samples for an intensity of 300 mJ/cm², a repetition rate of 10 Hz and an accumulation of 100 spectra per measuring point. The fluorescent signal is applied in arbitrary units versus the pulse number.

According to FIG. 6, a considerably prolonged period of irradiation being expressed in the number of pulses shows that a constant value of the LIF intensity is reached after a long phase of increase. Since under UV laser irradiation NBOH centers (650 nm LIF) and E'-centers (193 nm absorption) develop in the same way in synthetic fused silica with a high OH content it is concluded that the E'-centers being decisive for the absorption at 193 nm also reach a constant level. Therefore, the inventive procedure can be followed. In FIG. 6, a fourth sample with $H_2 = 3.3\cdot10^{18}$ cm$^{-3}$ is irradiated by an intensity of 300 mJ/cm$^{-3}$ once at a repetition rate of 50 Hz and then at a repetition rate of 10 Hz.

All elements presented in the description, the subsequent claims and the drawing can be decisive for the invention both as single elements and in any combination.

The invention claimed is:

1. Procedure for quantitative measurement of pulse laser stability of synthetic fused silica by a direct absorption measurement whereby suitability of the synthetic fused silica for use as an optical material exposed to laser pulses is determined, comprising:
   measuring the absorption of the fused silica for different light energy densities;
   determining a non-linear function $\alpha_1(H)$ from said measuring of the absorption of the fused silica for different light energy densities;
   irradiating the fused silica with a light energy density until reaching a constant absorption value;
   measuring the absorption of the fused silica for different light energy densities;
   determining a non-linear function $\alpha_2(H)$ from the measuring of the absorption of the fused silica for the last said different light energy densities; and
   determining an energy density dependent absorption increase from the difference of non-linear functions $\alpha_2(H)$ and $\alpha_1(H)$.

2. Procedure according to claim 1, wherein the irradiation is performed up to the saturation of the development of absorbing defect centers in the temperature range of T<200° K.

3. Procedure according to claim 2, wherein absorption, transmission and fluorescent measurements show that the saturation of the development of absorbing defect centers is reached.

4. The procedure according to claim 1, wherein said irradiating the fused silica with a light energy density until reaching a constant absorption value is done with an energy density of 5 mJ/cm² or higher.

* * * * *